(12) United States Patent
Han et al.

(10) Patent No.: US 11,459,554 B2
(45) Date of Patent: Oct. 4, 2022

(54) ENZYME COMPLEX COMPRISING BETA-AGARASE, KAPPA-CARRAGEENASE AND ANHYDRO-GALACTOSIDASE, AND USE THEREOF

(71) Applicant: KOREA UNIVERSITY RESEARCH AND BUSINESS FOUNDATION, Seoul (KR)

(72) Inventors: Sung Ok Han, Seoul (KR); Dae-Hee Kang, Gwangju-si (KR); Jeong-Eun Hyeon, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 226 days.

(21) Appl. No.: 16/065,896

(22) PCT Filed: Apr. 1, 2016

(86) PCT No.: PCT/KR2016/003389
§ 371 (c)(1),
(2) Date: Jun. 25, 2018

(87) PCT Pub. No.: WO2017/111208
PCT Pub. Date: Jun. 29, 2017

(65) Prior Publication Data
US 2019/0010475 A1    Jan. 10, 2019

(30) Foreign Application Priority Data

Dec. 23, 2015   (KR) .................. 10-2015-0184782

(51) Int. Cl.
*C12N 9/38* (2006.01)
*C12N 9/24* (2006.01)
(Continued)

(52) U.S. Cl.
CPC ......... *C12N 9/2468* (2013.01); *C12N 9/2402* (2013.01); *C12N 9/2437* (2013.01);
(Continued)

(58) Field of Classification Search
CPC .. C12N 9/2468; C12N 9/2402; C12N 9/2437; C12Y 302/01; C12Y 302/01081; C12Y 302/01083; C07K 2319/20; C07K 2319/70
See application file for complete search history.

(56) References Cited

FOREIGN PATENT DOCUMENTS

KR    10-2011-0044410 A     4/2011
KR       20110044410 A  *  4/2011
(Continued)

OTHER PUBLICATIONS

Jin et al., Marine Drugs, 2021, 271: 1-13. (Year: 2021).*
(Continued)

*Primary Examiner* — Allison M Fox
*Assistant Examiner* — Qing Xu
(74) *Attorney, Agent, or Firm* — NSIP Law

(57) ABSTRACT

The present invention relates to an enzyme complex which the following (i) to (iv) are combined: (i) chimeric beta-agarase formed by a fusion of beta-agarase and the dockerin module of endo-β-1,4-glucanase-B; (ii) chimeric kappa-carrageenase formed by a fusion of kappa-carrageenase and the dockerin module of endo-β-1,4-glucanase-B; (iii) chimeric anhydro-galactosidase formed by a fusion of anhydro-galactosidase and the dockerin module of endoβ-1,4-glucanase-B; and (iv) mini cellulose-binding protein A, and to a method of degrading red algal biomass using the same. According to the present invention, an enzymatic degradation process is applied for the production of agar degradation products, deviating from conventional methods that relied on physical and chemical pretreatment processes. Thus, the (Continued)

present invention will greatly contribute to efficiently converting marine algae into valuable products by use of a convenient, cost-effective, highly efficient and environmentally friendly degradation system while controlling the products.

7 Claims, 9 Drawing Sheets

Specification includes a Sequence Listing.

(51) Int. Cl.
  C12N 9/42   (2006.01)
  C12P 19/14  (2006.01)
  C12N 15/52  (2006.01)
(52) U.S. Cl.
  CPC .............. *C12N 15/52* (2013.01); *C12P 19/14* (2013.01); *C12Y 302/01* (2013.01); *C12Y 302/01081* (2013.01); *C12Y 302/01083* (2013.01); *C07K 2319/20* (2013.01); *C07K 2319/70* (2013.01)

(56) References Cited

FOREIGN PATENT DOCUMENTS

| KR | 10-2011-0045975 A | | 5/2011 |
| KR | 20110045975 A | * | 5/2011 |
| KR | 10-2012-0098247 A | | 9/2012 |
| KR | 10-1367348 B1 | | 2/2014 |
| KR | 101367348 B | * | 2/2014 |
| KR | 10-2014-0048516 A | | 4/2014 |
| KR | 10-2014-0099629 A | | 8/2014 |
| KR | 10-2014-0111240 A | | 9/2014 |
| KR | 10-2015-0028564 A | | 3/2015 |

OTHER PUBLICATIONS

Foong et al., Journal of General Microbiology, 1991, 137:1729-1736. (Year: 1991).*

Ximenes, E. F. F., "Hemicellulases and biotechnology", Recent Res Devel. in Microbiology, 1998, vol. 2 (7 pages in English).

Reiter, Wolf-Dieter, "Biosynthesis and properties of the plant cell wall", Current Opinion in Plant Biology, 2002, vol. 5, pp. 536-542 (7 pages in English).

Edward, Bayer A, et al. "The Cellulosomes: Multienzyme Machines for Degradation of Plant Cell Wall Polysaccharides", Annual Review of Microbiology, Feb. 2004 (42 pages in English).

NCBI Reference Sequence: WP_013994901.1, beta-agarase B [Zobellia galactanivorans], Zobellia galactanivorans, May 18, 2013 (1 page in English).

NCBI Reference Sequence: WP_010076241.1, endoglucanase [Clostridium cellulovorans], Clostridium cellulovorans, May 24, 2013 (1 page in English).

NCBI Reference Sequence: WP_013291799.1, cellulose-binding protein [Clostridium cellulovorans], Clostridium cellulovorans, May 26, 2013 (2 pages in English).

NCBI Reference Sequence: WP_013995985.1, glycosyhydrolase [Zobellia galactanivorans], Zobellia galactanivorans, May 27, 2013 (1 page in English).

UniProKB/Swiss-Prot: P43478.1, RecName: Full=Kappa-carrageenase; Flags: Precursor, Pseudoalteromonas carrageenovora, Nov. 26, 2014 (4 pages in English).

Kang, D.H., et al., "Efficient Enzymatic Degradation Process for Hydrolysis Activity of the Carrageenan from Red Algae in Marine Biomass", Journal of Biotechnology, 2014, vol. 192, pp. 108-113 (6 pages in English).

Hehemann, J.H., et al., "A sweet new wave: structures and mechanisms of enzymes that digest polysaccharides from marine algae", Current Opinion in Structural Biology, 2014, vol. 28, pp. 77-86 (10 pages in English).

Kang, D.H., et al., "Convenient Purification Method and Efficient Degradation of Red Algal Biomass by Protein Complexes Comprising of Various Hydrolytic Enzymes", (3 pages in English), Jan. 23, 2015.

Kang, D.H., et al., "Synergistic Effect of the Hydrolytic Enzyme Complexes Based on Cellulosome System for Efficient Utilization of Red Algae" 2015, pp. 491 (3 pages in English).

International Search Report dated Apr. 1, 2016 in International Application No. PCT/KR2016/003389 (3 pages in English).

Korean Notice of Allowance dated May 28, 2018 in corresponding Korean Patent Application No. 10-2015-0184782 (1 page in Korean).

* cited by examiner

Amount of converted sugar (Average)

Amount of converted sugar

SEQUENCE LISTING

```
<160> NUMBER OF SEQ ID NOS: 21

<210> SEQ ID NO 1
<211> LENGTH: 406
<212> TYPE: PRT
<213> ORGANISM: Artificial Sequence
<220> FEATURE:
<223> OTHER INFORMATION: Beta agarase

<400> SEQUENCE: 1

Gly Asp Asn Ser Lys Phe Asp Ser Ala Thr Asp Leu Pro Val Glu Gln
1               5                   10                  15

Glu Gln Glu Gln Glu Thr Glu Gln Glu Gly Glu Pro Glu Glu Ser Ser
            20                  25                  30

Glu Gln Asp Leu Val Glu Glu Val Asp Trp Lys Asp Ile Pro Val Pro
        35                  40                  45

Ala Asp Ala Gly Pro Asn Met Lys Trp Glu Phe Gln Glu Ile Ser Asp
    50                  55                  60
```

```
Asn Phe Glu Tyr Glu Ala Pro Ala Asp Asn Lys Gly Ser Glu Phe Leu
 65                  70                  75                  80

Glu Lys Trp Asp Asp Phe Tyr His Asn Ala Trp Ala Gly Pro Gly Leu
                 85                  90                  95

Thr Glu Trp Lys Arg Asp Arg Ser Tyr Val Ala Asp Gly Glu Leu Lys
            100                 105                 110

Met Trp Ala Thr Arg Lys Pro Gly Ser Asp Lys Ile Asn Met Gly Cys
        115                 120                 125

Ile Thr Ser Lys Thr Arg Val Val Tyr Pro Val Tyr Ile Glu Ala Arg
130                 135                 140

Ala Lys Val Met Asn Ser Thr Leu Ala Ser Asp Val Trp Leu Leu Ser
145                 150                 155                 160

Ala Asp Asp Thr Gln Glu Ile Asp Ile Leu Glu Ala Tyr Gly Ala Asp
                165                 170                 175

Tyr Ser Glu Ser Ala Gly Lys Asp His Ser Tyr Phe Ser Lys Lys Val
            180                 185                 190

His Ile Ser His His Val Phe Ile Arg Asp Pro Phe Gln Asp Tyr Gln
        195                 200                 205

Pro Lys Asp Ala Gly Ser Trp Phe Glu Asp Gly Thr Val Trp Asn Lys
210                 215                 220

Glu Phe His Arg Phe Gly Val Tyr Trp Arg Asp Pro Trp His Leu Glu
225                 230                 235                 240

Tyr Tyr Ile Asp Gly Val Leu Val Arg Thr Val Ser Gly Lys Asp Ile
                245                 250                 255

Ile Asp Pro Lys His Phe Thr Asn Thr Thr Asp Pro Gly Asn Thr Glu
            260                 265                 270

Ile Asp Thr Arg Thr Gly Leu Asn Lys Glu Met Asp Ile Ile Asn
        275                 280                 285

Thr Glu Asp Gln Thr Trp Arg Ser Ser Pro Ala Ser Gly Leu Gln Ser
290                 295                 300

Asn Thr Tyr Thr Pro Thr Asp Asn Glu Leu Ser Asn Ile Glu Asn Asn
305                 310                 315                 320

Thr Phe Gly Val Asp Trp Ile Arg Ile Tyr Lys Pro Val Glu Lys Gly
                325                 330                 335

Ser Ala Gly Ser Ala Ala Gly Ser Gly Glu Phe Asp Val Asn Lys Asp
            340                 345                 350

Gly Lys Val Asn Ala Ile Asp Tyr Ala Val Leu Lys Ser Ile Leu Leu
        355                 360                 365

Gly Thr Asn Thr Asn Val Asp Leu Ser Val Ser Asp Met Asn Lys Asp
370                 375                 380

Gly Lys Val Asn Ala Leu Asp Leu Ala Val Leu Lys Lys Met Leu Leu
385                 390                 395                 400

His His His His His His
            405

<210> SEQ ID NO 2
<211> LENGTH: 443
<212> TYPE: PRT
<213> ORGANISM: Artificial Sequence
<220> FEATURE:
<223> OTHER INFORMATION: Kappa carrageenase

<400> SEQUENCE: 2

Ala Ser Met Gln Pro Pro Ile Ala Lys Pro Gly Glu Thr Trp Ile Leu
 1               5                  10                  15
```

```
Gln Ala Lys Arg Ser Asp Glu Phe Asn Val Lys Asp Ala Thr Lys Trp
             20                  25                  30
Asn Phe Gln Thr Glu Asn Tyr Gly Val Trp Ser Trp Lys Asn Glu Asn
         35                  40                  45
Ala Thr Val Ser Asn Gly Lys Leu Lys Leu Thr Thr Lys Arg Glu Ser
 50                  55                  60
His Gln Arg Thr Phe Trp Asp Gly Cys Asn Gln Gln Val Ala Asn
 65                  70                  75                  80
Tyr Pro Leu Tyr Tyr Thr Ser Gly Val Ala Lys Ser Arg Ala Thr Gly
                 85                  90                  95
Asn Tyr Gly Tyr Tyr Glu Ala Arg Ile Lys Gly Ala Ser Thr Phe Pro
                100                 105                 110
Gly Val Ser Pro Ala Phe Trp Met Tyr Ser Thr Ile Asp Arg Ser Leu
             115                 120                 125
Thr Lys Glu Gly Asp Val Gln Tyr Ser Glu Ile Asp Val Val Glu Leu
 130                 135                 140
Thr Gln Lys Ser Ala Val Arg Glu Ser Asp His Asp Leu His Asn Ile
 145                 150                 155                 160
Val Val Lys Asn Gly Lys Pro Thr Trp Met Arg Pro Gly Ser Phe Pro
                 165                 170                 175
Gln Thr Asn His Asn Gly Tyr His Leu Pro Phe Asp Pro Arg Asn Asp
             180                 185                 190
Phe His Thr Tyr Gly Val Asn Val Thr Lys Asp Lys Ile Thr Trp Tyr
         195                 200                 205
Val Asp Gly Glu Ile Val Gly Glu Lys Asp Asn Leu Tyr Trp His Arg
 210                 215                 220
Gln Met Asn Leu Thr Leu Ser Gln Gly Leu Arg Ala Pro His Thr Gln
225                 230                 235                 240
Trp Lys Cys Asn Gln Phe Tyr Pro Ser Ala Asn Lys Ser Ala Glu Gly
                 245                 250                 255
Phe Pro Thr Ser Met Glu Val Asp Tyr Val Arg Thr Trp Val Lys Val
             260                 265                 270
Gly Asn Asn Asn Ser Ala Pro Gly Glu Gly Gln Ser Cys Pro Asn Thr
                 275                 280                 285
Phe Val Ala Val Asn Ser Val Gln Leu Ser Ala Ala Lys Gln Thr Leu
 290                 295                 300
Arg Lys Gly Gln Ser Thr Thr Leu Glu Ser Thr Val Leu Pro Asn Cys
305                 310                 315                 320
Ala Thr Asn Lys Lys Val Ile Tyr Ser Ser Asn Lys Asn Val Ala
                 325                 330                 335
Thr Val Asn Ser Ala Gly Val Val Lys Ala Lys Asn Lys Gly Thr Ala
             340                 345                 350
Thr Ile Thr Val Lys Thr Lys Asn Lys Gly Lys Ile Asp Lys Leu Thr
             355                 360                 365
Ile Ala Val Asn Gly Ser Ala Gly Ser Ala Ala Gly Ser Gly Glu Phe
 370                 375                 380
Asp Val Asn Lys Asp Gly Lys Val Asn Ala Ile Asp Tyr Ala Val Leu
 385                 390                 395                 400
Lys Ser Ile Leu Leu Gly Thr Asn Thr Asn Val Asp Leu Ser Val Ser
                 405                 410                 415
Asp Met Asn Lys Asp Gly Lys Val Asn Ala Leu Asp Leu Ala Val Leu
             420                 425                 430
```

```
Lys Lys Met Leu Leu His His His His His
            435                 440
```

<210> SEQ ID NO 3
<211> LENGTH: 461
<212> TYPE: PRT
<213> ORGANISM: Artificial Sequence
<220> FEATURE:
<223> OTHER INFORMATION: Anhydro-galactosidase

<400> SEQUENCE: 3

```
Met Asn Lys Tyr Ser Gln Phe Leu Ile Phe Ala Ala Val Leu Val Ser
1               5                   10                  15

Ala Cys Asn Ser Pro Lys Thr Thr Lys Glu Met Lys Ser Thr Asp Asp
            20                  25                  30

Cys Pro Glu Lys Val Thr Phe Thr Pro Glu Gln Ile Asp His Leu Gly
        35                  40                  45

Ile Thr Asp Thr Asn His Leu Ser Ala Ala Ser Lys Arg Ala Leu Lys
    50                  55                  60

Trp Pro Thr Asp Leu Gly Asn Glu Trp Phe Ile Gln Phe Gly Pro Leu
65                  70                  75                  80

Gln Pro Leu Lys Gly Asp Leu Ala Tyr Glu Glu Gly Val Val Arg Arg
                85                  90                  95

Asp Pro Ser Ala Ile Ile Lys Glu Asn Gly Lys Tyr Tyr Val Trp Tyr
            100                 105                 110

Ser Lys Ser Thr Gly Pro Thr Gln Gly Phe Gly Gly Asp Ile Glu Lys
        115                 120                 125

Asp Lys Val Phe Pro Trp Asp Arg Cys Asp Ile Trp Tyr Ala Thr Ser
    130                 135                 140

Glu Asp Gly Trp Thr Trp Lys Glu Glu Gly Pro Ala Val Thr Arg Gly
145                 150                 155                 160

Glu Lys Gly Ala Tyr Asp Asp Arg Ser Val Phe Thr Val Glu Ile Met
                165                 170                 175

Lys Trp Glu Asp Lys Tyr Tyr Leu Cys Tyr Gln Thr Val Lys Ser Pro
            180                 185                 190

Tyr Asn Val Arg Val Lys Asn Gln Val Gly Leu Ala Trp Ala Asp Ser
        195                 200                 205

Pro Asp Gly Pro Trp Thr Lys Ser Glu Glu Pro Ile Leu Ser Pro Ala
    210                 215                 220

Asp Asn Gly Val Trp Lys Gly Glu Glu Gln Asp Arg Phe Ala Val Ile
225                 230                 235                 240

Lys Lys Gly Asp Phe Asp Ser His Lys Val His Asp Pro Cys Ile Ile
                245                 250                 255

Pro Tyr Lys Gly Lys Phe Tyr Leu Tyr Tyr Lys Gly Glu Gln Met Gly
            260                 265                 270

Glu Ala Ile Thr Phe Gly Gly Arg Gln Ile Arg His Gly Val Ala Ile
        275                 280                 285

Ala Asp Asn Pro Lys Gly Pro Tyr Val Lys Ser Pro Tyr Asn Pro Ile
    290                 295                 300

Ser Asn Ser Gly His Glu Ile Cys Val Trp Pro Tyr Asn Gly Gly Ile
305                 310                 315                 320

Ala Ser Leu Ile Thr Thr Asp Gly Pro Glu Lys Asn Thr Ile Gln Trp
                325                 330                 335

Ala Pro Asp Gly Ile Asn Phe Glu Ile Lys Ser Val Ile Pro Gly Val
            340                 345                 350
```

```
Asn Ala His Ala Ile Gly Leu Asn Arg Thr Ala Asp Val Glu Lys Glu
            355                 360                 365

Pro Thr Glu Ile Leu Arg Trp Gly Leu Thr His Ile Tyr Asn Asn Gly
370                 375                 380

Asp Tyr Gln Ser Ile Met Arg Phe Ser Ser Glu Arg Lys Thr Arg His
385                 390                 395                 400

Val Ala Lys Gly Val Lys Lys Gln Asp Val Asn Lys Asp Gly Lys Val
                405                 410                 415

Asn Ala Ile Asp Tyr Ala Val Leu Lys Ser Ile Leu Leu Gly Thr Asn
            420                 425                 430

Thr Asn Val Asp Leu Ser Val Ser Asp Met Asn Lys Asp Gly Lys Val
            435                 440                 445

Asn Ala Leu Asp Leu Ala Val Leu Lys Lys Met Leu Leu
450                 455                 460

<210> SEQ ID NO 4
<211> LENGTH: 441
<212> TYPE: PRT
<213> ORGANISM: Artificial Sequence
<220> FEATURE:
<223> OTHER INFORMATION: endo-beta-1, 4-glucanase

<400> SEQUENCE: 4

Met Asn Lys Arg Leu Ser Arg Gly Lys Ile Ser Leu Leu Ala Ser Val
1               5                   10                  15

Phe Val Thr Thr Thr Phe Met Gly Gly Val Asn Val Leu Ala Ser Thr
                20                  25                  30

Ala Lys Thr Gly Ile Arg Asp Ile Thr Ser Gln Gln Val Lys Glu
            35                  40                  45

Met Lys Val Gly Trp Asn Leu Gly Asn Thr Met Asp Ala Thr Gly Gly
        50                  55                  60

Glu Thr Asn Trp Gly Asn Pro Leu Thr Thr His Ala Met Ile Asp Lys
65                  70                  75                  80

Val Lys Ala Ala Gly Phe Asn Thr Leu Arg Leu Pro Ile Thr Trp Asp
                85                  90                  95

Gly His Ile Gly Ala Ala Pro Asp Tyr Ala Ile Asp Ala Thr Trp Met
            100                 105                 110

Asn Arg Val Glu Glu Ile Ala Asn Tyr Ala Phe Asp Asn Asn Met Tyr
        115                 120                 125

Val Ile Ile Asn Leu His His Glu Asp Gly Trp Leu Lys Pro Tyr Tyr
130                 135                 140

Ala Asn Glu Ala Glu Val Lys Ala Lys Ile Thr Lys Val Trp Thr Gln
145                 150                 155                 160

Ile Ala Asn Arg Phe Lys Asp Tyr Gly Asp Tyr Leu Ile Phe Glu Thr
                165                 170                 175

Met Asn Glu Pro Arg Pro Val Gly Ala Ala Asp Glu Trp Ser Gly Gly
            180                 185                 190

Ser Tyr Glu Asn Arg Asp Met Val Asn Arg Tyr Asn Leu Thr Ala Val
        195                 200                 205

Asn Thr Ile Arg Ala Thr Gly Gly Asn Asn Ala Leu Arg His Ile Met
210                 215                 220

Val Pro Thr Leu Ala Ala Ala Ala Leu Ser Thr Thr Met Asn Asp Tyr
225                 230                 235                 240

Ile Val Pro Asn Asn Asp Ser Arg Val Ile Val Ser Leu His Met Tyr
                245                 250                 255
```

Ser Pro Tyr Phe Phe Ser Ala Asp Leu Thr Ser Gln Trp Thr Ala
            260                 265                 270

Thr Trp Gly Ser Asp Ala Asp Lys Ala Ala Leu Ser Ala Asp Phe Asp
        275                 280                 285

Ala Val Tyr Asn Lys Phe Val Lys Asn Gly Arg Ala Val Val Ile Gly
        290                 295                 300

Glu Met Gly Thr Ile Asn Lys Asn Asn Leu Asp Ser Arg Val Lys His
305                 310                 315                 320

Ala Glu Tyr Tyr Ala Lys Glu Ala Thr Val Arg Gly Ile Thr Pro Ile
                325                 330                 335

Trp Trp Asp Asn Gly Tyr Cys Val Ala Gly Lys Glu Gln Thr Phe Gly
            340                 345                 350

Ile Phe Asn Arg Lys Asn Leu Thr Trp Cys Cys Pro Glu Val Met Gln
        355                 360                 365

Ala Phe Ile Arg Gly Ala Gly Ala Thr Gln Thr Gln Thr Ser Tyr Ser
        370                 375                 380

Leu Gly Asp Val Asn Lys Asp Gly Lys Val Asn Ala Ile Asp Tyr Ala
385                 390                 395                 400

Val Leu Lys Ser Ile Leu Leu Gly Thr Asn Thr Asn Val Asp Leu Ser
                405                 410                 415

Val Ser Asp Met Asn Lys Asp Gly Lys Val Asn Ala Leu Asp Leu Ala
            420                 425                 430

Val Leu Lys Lys Met Leu Leu Ser Leu
            435                 440

<210> SEQ ID NO 5
<211> LENGTH: 549
<212> TYPE: PRT
<213> ORGANISM: Artificial Sequence
<220> FEATURE:
<223> OTHER INFORMATION: cellulose binding protein A

<400> SEQUENCE: 5

Ala Ala Thr Ser Ser Met Ser Val Glu Phe Tyr Asn Ser Asn Lys Ser
1               5                   10                  15

Ala Gln Thr Asn Ser Ile Thr Pro Ile Ile Lys Ile Thr Asn Thr Ser
            20                  25                  30

Asp Ser Asp Leu Asn Leu Asn Asp Val Lys Val Arg Tyr Tyr Tyr Thr
        35                  40                  45

Ser Asp Gly Thr Gln Gly Gln Thr Phe Trp Cys Asp His Ala Gly Ala
    50                  55                  60

Leu Leu Gly Asn Ser Tyr Val Asp Asn Thr Ser Lys Val Thr Ala Asn
65                  70                  75                  80

Phe Val Lys Glu Thr Ala Ser Pro Thr Ser Thr Tyr Asp Thr Tyr Val
                85                  90                  95

Glu Phe Gly Phe Ala Ser Gly Ala Ala Thr Leu Lys Lys Gly Gln Phe
            100                 105                 110

Ile Thr Ile Gln Gly Arg Ile Thr Lys Ser Asp Trp Ser Asn Tyr Thr
        115                 120                 125

Gln Thr Asn Asp Tyr Ser Phe Asp Ala Ser Ser Ser Thr Pro Val Val
    130                 135                 140

Asn Pro Lys Val Thr Gly Tyr Ile Gly Gly Ala Lys Val Leu Gly Thr
145                 150                 155                 160

Ala Pro Gly Pro Asp Val Pro Ser Ser Ile Ile Asn Pro Thr Ser Ala
                165                 170                 175

```
Thr Phe Asp Lys Asn Val Thr Lys Gln Ala Asp Val Lys Thr Thr Met
            180                 185                 190
Thr Leu Asn Gly Asn Thr Phe Lys Thr Ile Thr Asp Ala Asn Gly Thr
        195                 200                 205
Ala Leu Asn Ala Ser Thr Asp Tyr Ser Val Ser Gly Asn Asp Val Thr
    210                 215                 220
Ile Ser Lys Ala Tyr Leu Ala Lys Gln Ser Val Gly Thr Thr Thr Leu
225                 230                 235                 240
Asn Phe Asn Phe Ser Ala Gly Asn Pro Gln Lys Leu Val Ile Thr Val
            245                 250                 255
Val Asp Thr Pro Val Glu Ala Val Thr Ala Thr Ile Gly Lys Val Gln
        260                 265                 270
Val Asn Ala Gly Glu Thr Val Ala Val Pro Val Asn Leu Thr Lys Val
    275                 280                 285
Pro Ala Ala Gly Leu Ala Thr Ile Glu Leu Pro Leu Thr Phe Asp Ser
290                 295                 300
Ala Ser Leu Glu Val Val Ser Ile Thr Ala Gly Asp Ile Val Leu Asn
305                 310                 315                 320
Pro Ser Val Asn Phe Ser Ser Thr Val Ser Gly Ser Thr Ile Lys Leu
            325                 330                 335
Leu Phe Leu Asp Asp Thr Leu Gly Ser Gln Leu Ile Thr Lys Asp Gly
        340                 345                 350
Val Phe Ala Thr Ile Thr Phe Lys Ala Lys Ala Ile Thr Gly Thr Thr
    355                 360                 365
Ala Lys Val Thr Ser Val Lys Leu Ala Gly Thr Pro Val Val Gly Asp
370                 375                 380
Ala Gln Leu Gln Glu Lys Pro Cys Ala Val Asn Pro Gly Thr Val Thr
385                 390                 395                 400
Ile Asn Pro Ile Asp Asn Arg Met Gln Ile Ser Val Gly Thr Ala Thr
            405                 410                 415
Val Lys Ala Gly Glu Ile Ala Ala Val Pro Val Thr Leu Thr Ser Val
        420                 425                 430
Pro Ser Thr Gly Ile Ala Thr Ala Glu Ala Gln Val Ser Phe Asp Ala
    435                 440                 445
Thr Leu Leu Glu Val Ala Ser Val Thr Ala Gly Asp Ile Val Leu Asn
450                 455                 460
Pro Thr Val Asn Phe Ser Tyr Thr Val Asn Gly Asn Val Ile Lys Leu
465                 470                 475                 480
Leu Phe Leu Asp Asp Thr Leu Gly Ser Gln Leu Ile Ser Lys Asp Gly
            485                 490                 495
Val Phe Val Thr Ile Asn Phe Lys Ala Lys Ala Val Thr Ser Thr Val
        500                 505                 510
Thr Thr Pro Val Thr Val Ser Gly Thr Pro Val Phe Ala Asp Gly Thr
    515                 520                 525
Leu Ala Glu Val Gln Ser Lys Thr Ala Ala Gly Ser Val Thr Ile Asn
530                 535                 540

Ile Gly Asp Pro Ile
545

<210> SEQ ID NO 6
<211> LENGTH: 22
<212> TYPE: DNA
<213> ORGANISM: Artificial Sequence
<220> FEATURE:
<223> OTHER INFORMATION: primer
```

-continued

```
<400> SEQUENCE: 6
gcgcggatcc attcaccgca at                                              22

<210> SEQ ID NO 7
<211> LENGTH: 26
<212> TYPE: DNA
<213> ORGANISM: Artificial Sequence
<220> FEATURE:
<223> OTHER INFORMATION: primer

<400> SEQUENCE: 7
atatccatgg atgcatctat gcaacc                                          26

<210> SEQ ID NO 8
<211> LENGTH: 30
<212> TYPE: DNA
<213> ORGANISM: Artificial Sequence
<220> FEATURE:
<223> OTHER INFORMATION: primer

<400> SEQUENCE: 8
ccatggattc tcaatcggct attaaaagta                                      30

<210> SEQ ID NO 9
<211> LENGTH: 31
<212> TYPE: DNA
<213> ORGANISM: Artificial Sequence
<220> FEATURE:
<223> OTHER INFORMATION: primer

<400> SEQUENCE: 9
ggatccacga acactatgac gtgaattttc t                                    31

<210> SEQ ID NO 10
<211> LENGTH: 33
<212> TYPE: DNA
<213> ORGANISM: Artificial Sequence
<220> FEATURE:
<223> OTHER INFORMATION: primer

<400> SEQUENCE: 10
gcgcgagctc cggcgacaat tcaaaatttg ata                                  33

<210> SEQ ID NO 11
<211> LENGTH: 32
<212> TYPE: DNA
<213> ORGANISM: Artificial Sequence
<220> FEATURE:
<223> OTHER INFORMATION: primer

<400> SEQUENCE: 11
cagcggatcc tttctctaca ggtttataga tc                                   32

<210> SEQ ID NO 12
<211> LENGTH: 37
<212> TYPE: DNA
<213> ORGANISM: Artificial Sequence
<220> FEATURE:
<223> OTHER INFORMATION: primer

<400> SEQUENCE: 12
gcgcgaattc gatgaacaaa tactcccaat ttttaat                              37

<210> SEQ ID NO 13
```

```
<211> LENGTH: 33
<212> TYPE: DNA
<213> ORGANISM: Artificial Sequence
<220> FEATURE:
<223> OTHER INFORMATION: primer

<400> SEQUENCE: 13
tgttaacatc ttgttttttt actcctttag cta                                    33

<210> SEQ ID NO 14
<211> LENGTH: 23
<212> TYPE: DNA
<213> ORGANISM: Artificial Sequence
<220> FEATURE:
<223> OTHER INFORMATION: primer

<400> SEQUENCE: 14
ggatccgcag cgacatcatc aat                                               23

<210> SEQ ID NO 15
<211> LENGTH: 34
<212> TYPE: DNA
<213> ORGANISM: Artificial Sequence
<220> FEATURE:
<223> OTHER INFORMATION: primer

<400> SEQUENCE: 15
gcgcggtacc gctataggat ctccaatatt tatt                                   34

<210> SEQ ID NO 16
<211> LENGTH: 26
<212> TYPE: DNA
<213> ORGANISM: Artificial Sequence
<220> FEATURE:
<223> OTHER INFORMATION: Primer

<400> SEQUENCE: 16
atatccatgg atgcatctat gcaacc                                            26

<210> SEQ ID NO 17
<211> LENGTH: 22
<212> TYPE: DNA
<213> ORGANISM: Artificial Sequence
<220> FEATURE:
<223> OTHER INFORMATION: Primer

<400> SEQUENCE: 17
gcgcggatcc attcaccgca at                                                22

<210> SEQ ID NO 18
<211> LENGTH: 33
<212> TYPE: DNA
<213> ORGANISM: Artificial Sequence
<220> FEATURE:
<223> OTHER INFORMATION: Primer

<400> SEQUENCE: 18
gcgcgagctc cggcgacaat tcaaaatttg ata                                    33

<210> SEQ ID NO 19
<211> LENGTH: 49
<212> TYPE: DNA
<213> ORGANISM: Artificial Sequence
<220> FEATURE:
<223> OTHER INFORMATION: Primer

<400> SEQUENCE: 19
```

```
gcgcggccgc tcaatgatga tgatgatgat gtaaaagcat tttttttaag         49

<210> SEQ ID NO 20
<211> LENGTH: 37
<212> TYPE: DNA
<213> ORGANISM: Artificial Sequence
<220> FEATURE:
<223> OTHER INFORMATION: Primer

<400> SEQUENCE: 20
gcgcgaattc gatgaacaaa tactcccaat ttttaat                       37

<210> SEQ ID NO 21
<211> LENGTH: 36
<212> TYPE: DNA
<213> ORGANISM: Artificial Sequence
<220> FEATURE:
<223> OTHER INFORMATION: Primer

<400> SEQUENCE: 21
gcgcaagctt taaaagcatt tttttaagaa cagcta                        36
```

ENZYME COMPLEX COMPRISING BETA-AGARASE, KAPPA-CARRAGEENASE AND ANHYDRO-GALACTOSIDASE, AND USE THEREOF

CROSS REFERENCE TO RELATED APPLICATION(S)

This application is a U.S. National Stage Application of International Application No. PCT/KR2016/003389, filed on Apr. 1, 2016, which claims the benefit under 35 USC 119(a) and 365(b) of Korean Patent Application No. 10-2015-0184782, filed on Dec. 23, 2015, in the Korean Intellectual Property Office, the entire disclosures of which are incorporated herein by reference for all purposes.

TECHNICAL FIELD

The present invention relates to an enzyme complex which (i) chimeric beta-agarase formed by a fusion of beta-agarase and the dockerin module of endo-β-1,4-glucanase-B; (ii) chimeric kappa-carrageenase formed by a fusion of kappa-carrageenase and the dockerin module of endo-β-1,4-glucanase-B; (iii) chimeric anhydro-galactosidase formed by a fusion of anhydro-galactosidase and the dockerin module of endo-β-1,4-glucanase-B; and (iv) mini cellulose-binding protein A; are combined, and to a method of degrading red algal biomass using the same.

INCORPORATION-BY-REFERENCE OF MATERIAL SUBMITTED BY U.S.P.T.O. EFS-WEB

The instant application contains a Sequence Listing which is being submitted in computer readable form via the United States Patent and Trademark Office eFS-WEB system and which is hereby incorporated by reference in its entirety for all purposes. The txt file submitted herewith contains a 23 KB file (MISC20210805_0181650003_Sequence Listingas-Filed.txt).

BACKGROUND ART

Agar is a polysaccharide found mainly in the cell walls of red algae. It is a kind of dietary fiber source. It is mainly used in a solid medium for microbial culture, and is used as a stabilizer in confectionery and meat processing, and is also as a gelling agent in cosmetics or foods. Such agar consists of about 70% agarose and about 30% agaropectin. The agarose is a neutral polysaccharide, and contains alternating α-1,3 and β-1,4 linkages between galactose units. Meanwhile, agaropectin is an acidic polysaccharide containing sulfate groups (particularly sulfate), gluconic acid or pyruvate conjugated to agarose. Among the components other than agarose of red algae, carrageenan is a linear polysaccharide which is a galactan composed of galactose residues linked by alternating α-1,3 and β-1,4 linkages. Carrageenan is structurally the same as agarose, but differs from agarose in that 3,6-anhydro-D-galactose and sulfate ester groups are bonded to all or some galactan units and in that there are structural modifications depending on the positions of residues. Representative carrageenan types include kappa, iota and lambda carrageenans.

Agarase, an enzyme that degrades agar, hydrolyzes β-1,4 linkages in the galactose polymer of agarose and hydrolyzes into neoagarooligosaccharides, thereby producing disaccharides or trisaccharides containing galactose residues. Furthermore, kappa-carrageenase, an enzyme that degrades kappa-carrageenan, cleaves the 3, 4-linked galactose unit of kappa-carrageenan, thereby producing disaccharides containing carrageenan residues.

Moreover, the novel enzyme anhydro-galactosidase act to cleave the 1,3-α-3,6-l-galacosidic linkages of neoagarooligosaccharides produced by hydrolysis with beta-agarase and kappa-carrageenase, thereby producing fermentable monosaccharides.

Meanwhile, lignocellulose is a constituent of the cell wall of plants and is composed of a complex of cellulose and hemicellulose. Cellulose is a β-1,4-glucose complex and is the most abundant renewable material in nature (Reiter et al. CurrOpinPlant Biol 5: 536, 1998). Although the chemical structure of cellulose is simple, the activities of several different enzymes are required for efficient degradation of cellulose (Ximenes et al. Hemicellulases and biotechnology. Recent Res Develop Microbiol 2:165, 1998). Hemicellulose includes xylan which is β-1,4-xylose, β-1,4 glucose, glucomannan which is mannose, and the like. Most anaerobic microorganisms capable of degrading cellulose form an enzyme complex, called cellulosome (Roy H. Doi, The Chemical Record 1:24, 2001). Cellulosomes act on a variety of substrates such as crystalline cellulose, xylan, mannan, and pectin, and are composed of cellulosome forming enzymes and scaffold proteins. Formation of cellulosome is achieved by binding of the dockerin module of one cellulosome forming enzyme to one of several cohesion modules of the scaffold protein. All cellulosome forming enzymes have dockerin modules, and enzymes having no dockerin module are non-cellulosome forming enzymes (Bayer et al. Annual Review of Microbiol 58:521, 2004).

In the prior art, studies have been conducted to improve agar degradation ability by an enzyme complex containing the agar-degrading enzyme beta-agarase, and studies have been conducted to improve carrageenan degradation ability by an enzyme complex containing kappa-carrageenase and lambda-carrageenase, which are carrageenan-degrading enzymes.

Accordingly, the present inventors have made extensive efforts to develop a highly active hydrolytic enzyme complex containing a combination of existing enzymes and a novel enzyme, and as a result, have found that an enzyme complex containing beta-agarase, kappa-carrageenase and anhydro-galactosidase exhibits a high ability to degrade red algal biomass, thereby completing the present invention.

The information disclosed in the Background Art section is only for the enhancement of understanding of the background of the present invention, and therefore may not contain information that forms a prior art that would already be known to a person of ordinary skill in the art.

DISCLOSURE OF INVENTION

Technical Problem

It is an object of the present invention to provide an enzyme complex having an excellent ability to degrade red algal biomass, which contains beta-agarase, kappa carrageenase, and anhydrous galactosidase.

Another object of the present invention is to provide a recombinant microorganism having a gene encoding the enzyme complex introduced therein.

Still another object of the present invention is to provide a method for preparing the enzyme complex.

Yet another object of the present invention is to provide a method of degrading red algal biomass using the enzyme complex.

Technical Solution

To achieve the above object, the present invention provides an enzyme complex which the following (i) to (iv) are combined:
(i) chimeric beta-agarase formed by a fusion of beta-agarase and the dockerin module of endo-β-1,4-glucanase-B;
(ii) chimeric kappa-carrageenase formed by a fusion of kappa-carrageenase and the dockerin module of endo-β-1,4-glucanase-B;
(iii) chimeric anhydro-galactosidase formed by a fusion of anhydro-galactosidase and the dockerin module of endo-β-1,4-glucanase-B; and
(iv) mini cellulose-binding protein A.

The present invention also provides a recombinant microorganism having introduced therein a gene encoding chimeric beta-agarase formed by a fusion of beta-agarase and the dockerin module of endo-β-1,4-glucanase-B, a gene encoding chimeric kappa-carrageenase formed by a fusion of kappa-carrageenase and the dockerin module of endo-β-1,4-glucanase-B, and a gene encoding chimeric anhydro-galactosidase formed by a fusion of anhydro-galactosidase and the dockerin module of endo-β-1,4-glucanase-B.

The present invention also provides a method for preparing the enzyme complex.

The present invention also provides a method of degrading red algal biomass using the enzyme complex.

BEST MODE FOR CARRYING OUT THE INVENTION

Figure 1:
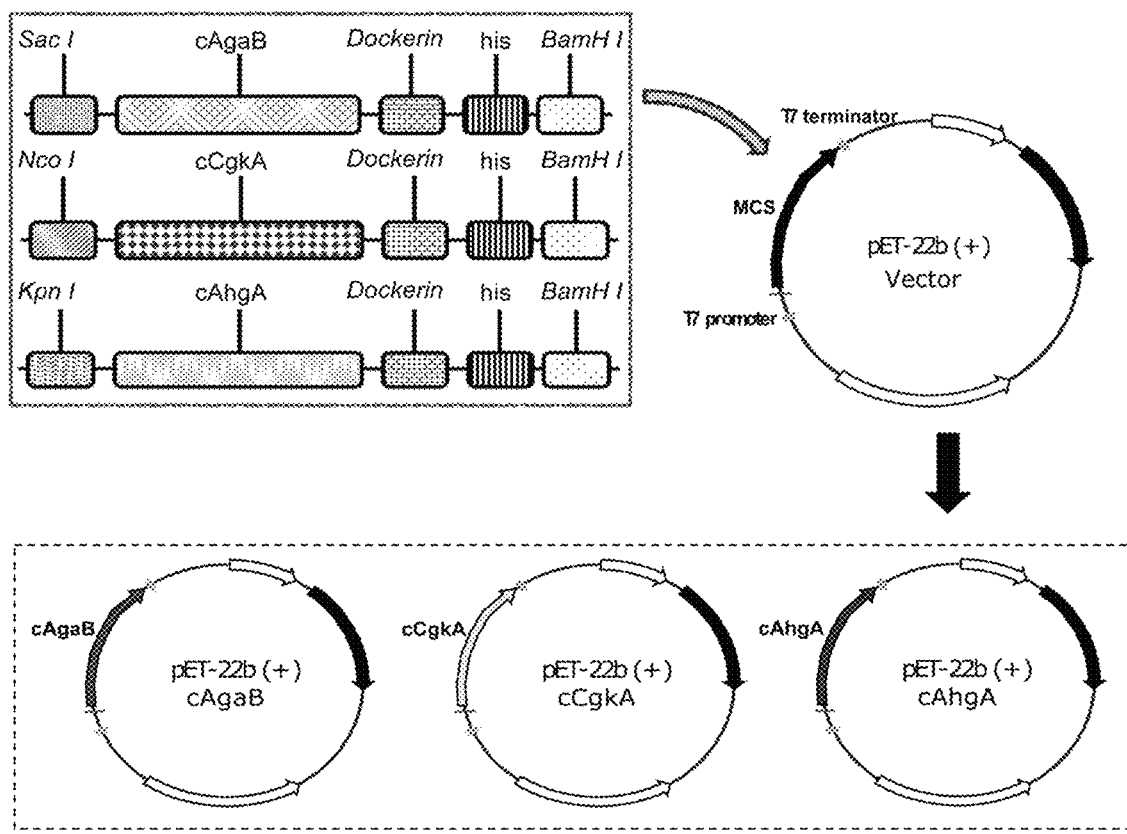
FIG. 1 is a schematic view showing the recombinant vectors pET22(+)cCgkA, pET22(+)cAgaB, pET22(+)cAhgA, and pET22b(+)mCbpA according to the present invention, which have inserted therein chimeric kappa-carrageenase gene, chimeric beta-agarase gene, chimeric anhydro-galactosidase gene and mini scaffold protein miniCbpA gene, respectively.

Unless defined otherwise, all the technical and scientific terms used herein have the same meaning as those generally understood by one of ordinary skill in the art to which the invention pertains. Generally, the nomenclature used herein and the experiment methods, which will be described below, are those well known and commonly employed in the art.

In the present invention, studies have been conducted to allow an enzyme complex to have more effective hydrolytic ability for agar degradation by use of the agar-degrading enzyme beta-agarase, the carrageenan-degrading enzyme kappa-carrageenase and the novel enzyme anhydro-galactosidase. The enzyme complexes developed in the prior art exhibited the respective hydrolytic activities on limited substrates by enzyme-substrate specificity. However, the present invention applies the complex technology developed in the prior art, and shows a technology related to highly active hydrolytic enzyme complexes having improved hydrolytic ability compared to the prior art technology by stepwise hydrolytic processes of different enzymes for agar hydrolysis. This suggests that the highly active hydrolytic enzyme complex according to the present invention can efficiently convert low-value-added agar into high-value-added fermentable monosaccharides and anhydro-galactose. Therefore, in one aspect, the present invention is directed to an enzyme complex which the following (i) to (iv) are combined:
(i) chimeric beta-agarase formed by a fusion of beta-agarase and the dockerin module of endo-β-1,4-glucanase-B;
(ii) chimeric kappa-carrageenase formed by a fusion of kappa-carrageenase and the dockerin module of endo-β-1,4-glucanase-B;
(iii) chimeric anhydro-galactosidase formed by a fusion of anhydro-galactosidase and the dockerin module of endo-β-1,4-glucanase-B; and
(iv) mini cellulose-binding protein A.

In the present invention, the anhydro-galactosidase may be derived from *Zobellia galactanivorans*, *Saccharophagus degradans* or *Agarivorans gilvus*.

In the present invention, "dockerin module of *Clostridium* spp. strains" means the module of cellulosomal cellulase protein that forms the enzyme complex cellulosome by interaction with a cohesin module which is a portion of the cellulose-binding protein of *Clostridium* spp.

In the present invention, "mini cellulose-binding protein A (mCbpA)" means a protein that binds to cellulose making the primary scaffolding subunit of cellulosome. The mini cellulose-binding protein A (mCbpA) that is used in the present invention is a mini cellulose-binding protein having one carbohydrate binding module (CBM) and two cohesin modules in cellulose-binding protein A (CbpA) which is one of the cellulose-binding proteins of *Clostridium* spp.

The fundamental structure of a cellulosomal complex is based on a primary scaffolding subunit having one carbohydrate binding module (CBM) and contains a combination of the enzyme subunits of cellulase or hemicellulase having catalytic modules. To form this structure, nine cohesin modules in the primary scaffolding subunit strongly bind to the dockerin module of each enzyme subunit by protein-protein interaction.

In another aspect, the present invention is directed to a recombinant microorganism having introduced therein a gene encoding chimeric beta-agarase formed by a fusion of beta-agarase and the dockerin module of endo-β-1,4-glucanase-B, a gene encoding chimeric kappa-carrageenase formed by a fusion of kappa-carrageenase and the dockerin module of endo-β-1,4-glucanase-B, and a gene encoding chimeric anhydro-galactosidase formed by a fusion of anhydro-galactosidase and the dockerin module of endo-β-1,4-glucanase-B.

As used herein, the term "vector" means a DNA construct containing a DNA sequence operably linked to a suitable control sequence capable of effecting the expression of the DNA in a suitable host. The vector may be a plasmid, a phage particle, or simply a potential genomic insert. Once incorporated into a suitable host, the vector may replicate and function independently of the host genome, or may in some instances, integrate into the genome itself. In the present specification, "plasmid" and "vector" are sometimes used interchangeably, as the plasmid is the most commonly used form of vector. However, the present invention is intended to include other types of vectors with the same function as that would be known or known in the art.

As used herein, the term "expression control sequence" refers to the DNA sequences essential for the expression of the coding sequence operably linked in a particular host organism. Such control sequences include a promoter for performing transcription, any operator sequence for controlling such transcription, a sequence for encoding a suitable mRNA ribosomal binding site, and a sequence for controlling the termination of transcription and translation. For example, control sequences suitable for prokaryotes include a promoter, an operator sequence, and a ribosomal binding site. Eukaryotic cells include promoters, polyadenylation signals, and enhancers. The factor having the greatest effect on the expression level of the gene in the plasmid is a promoter. SRα promoter, cytomegalovirus promoter and the like are preferably used as a promoter for high expression.

To express the DNA sequence of the present invention, any of a wide variety of expression control sequences may be used in the vector. Examples of useful expression control sequences include, for example, the early and late promoters of SV40 or adenovirus, the lac system, the trp system, the TAC or TRC system, T3 and T7 promoters, the major operator and promoter regions of phage lambda, the control regions of fd coat protein, the promoter for 3-phosphoglycerate kinase or other glycolytic enzymes, the promoters of phosphatase, the promoters of the yeast α-mating system, and other sequences known to control the expression of genes of prokaryotic or eukaryotic cells or their viruses, and various combinations thereof.

A nucleic acid is operably linked when it is placed in a functional relationship with another nucleic acid sequence. The nucleotide sequence may be a gene and a control sequence(s) linked to be capable of expressing the gene when it binds to a control sequence(s) (e.g., transcription-activating protein). For example, DNA for a pre-sequence or a secretory leader is operably linked to DNA encoding polypeptide when expressed as pre-protein participating in secretion of polypeptide; a promoter or an enhancer is operably linked to a coding sequence when affecting the transcription of the sequence; and a RBS is operably linked to a coding sequence when affecting the transcription of the sequence, or to a coding sequence when arranged to facilitate translation. Generally, the term "operably linked" means that the DNA linked sequences are contiguous, and in the case of the secretory leader, are contiguous and present in a reading frame. However, an enhancer is not necessarily contiguous. The linkage between these sequences is performed by ligation at a convenient restriction enzyme site. However, when the site does not exist, a synthetic oligonucleotide adaptor or a linker is used according to a conventional method.

The term "expression vector" as used herein generally means a recombinant carrier as a double-stranded DNA fragment into which a heterologous DNA fragment is inserted. Here, the heterologous DNA means a hetero-type DNA, which is not naturally found in a host cell. The expression vector may be self-replicable regardless of host chromosomal DNA once in a host cell, and may produce several copies of the vector and (heterologous) DNA inserted thereinto.

As is well known in the art, in order to increase the expression level of a transfected gene in a host cell, a corresponding gene should be operably linked to transcription and translation expression control sequences which are operated in a selected expression host. Preferably, the expression control sequences and the corresponding gene are included in one expression vector together with a bacterial selection marker and a replication origin.

The host cell transformed or transfected by the aforementioned expression vector constitutes another aspect of the present invention. As used herein, the term "transformation" means that DNA can be replicated as a factor outside of chromosome or by means of completion of the entire chromosome by introducing DNA as a host. Of course, it should be understood that all vectors and expression control sequences do not equally function to express DNA sequences according to the present invention. Similarly, all hosts do not equally function with respect to the same expression system. However, one skilled in the art may appropriately select from among various vectors, expression control sequences, and hosts without either departing from the scope of the present invention or bearing excessive experimental burden.

For example, a vector must be selected considering a host cell, because the vector must be replicated in the host cell. Specifically, the copy number of the vector, the ability of regulating the copy number and the expression of other protein encoded by the corresponding vector (e.g., the expression of an antibiotic marker) should also be considered. Also, an expression control sequence may be selected taking several factors into consideration. For example, relative strength, control capacity and compatibility with the DNA sequence of the present invention of the sequence should be deliberated particularly with respect to possible secondary structures. Further, the selection of a unicellular host cell may be made under consideration of compatibility with a selected vector, toxicity of a product encoded by a DNA sequence, secretory nature of the product, ability to correctly fold a polypeptide, fermentation or cultivation requirements, ability to ensure easy purification of a product encoded by a DNA sequence, or the like. Within the scope of these parameters, one of ordinary skill in the art may select various vectors/expression control sequences/host combinations that can express the DNA sequences of the invention in either large scale animal culture or fermentation. In cloning the cDNA of a protein by the expression cloning strategy, screening procedures such as a binding method, a panning method, and a film emulsion method can be used.

In still another aspect, the present invention is directed to a method for preparing the enzyme complex.

In yet another aspect, the present invention is directed to a method of degrading red algal biomass using the enzyme complex.

In the present invention, the red algal biomass may be agar or carrageenan.

In addition, in the present invention, purification of hydrolytic enzyme complexes using the carbohydrate binding module (CBM) was performed, and it was shown that the obtained hydrolytic enzyme complex containing a combination of mCbpA, cCgkA, cAgaB, and cAhgA showed a reducing sugar production, which is 3.9-fold higher than that of pure beta-agarase (cAgaB), from agar and carrageenan substrates.

EXAMPLES

Hereinafter, the present invention will be described in further detail with reference to examples. It will be obvious to a person having ordinary skill in the art that these examples are for illustrative purposes only and are not to be construed to limit the scope of the present invention.

Example 1: Amplification of Dockerin Domain Gene of Cellulase, and Kappa-Carrageenase, Beta-Agarase and Anhydro-Galactosidase Genes For cloning the dockerin domain gene of cellulase for formation of a complex of agar-degrading enzymes, with reference to SEQ ID NO: 4 which is the nucleotide sequence of the dockerin domain of the endo-β-1,4-glucanase-B gene from the genomic DNA of Clostridium cellulovorans, primers were designed and synthesized such that the 5' end of the forward primer of SEQ ID NO: 6 contained the 10-bp C-terminal sequence of each of kappa-carrageenase CgkA gene derived from Pseudoalteromonas carrageenovora, beta-agarase AgaB gene derived from Zobellia galactanivorans, and anhydro-galactosidase AhgA gene, and such that a restriction enzyme recognition sequence was inserted in the 5' end of the reverse primer of SEQ ID NO: 7. Using the synthesized primers, PCR was performed. As a result, a 212-bp PCR band containing the dockerin domain gene of the endo-β-1,4-glucanase-B gene could be observed.

```
Primer SEQ ID NO: 6:
GCGCggatccATTCACCGCAAT

Primer SEQ ID NO: 7:
ATATccatggATGCATCTATGCAACC
```

For cloning the chimeric kappa-carrageenase cCgkA gene derived from Pseudoalteromonas carrageenovora, with reference to a nucleotide sequence excluding a signal peptide region from the genomic DNA of Zobellia galactanivorans, primers were designed and synthesized such that a restriction enzyme SacI recognition sequence was inserted in the 5' end of the forward primer of SEQ ID NO: 8, and such that the 5' end of the reverse primer of SEQ ID NO: 9 contained a restriction enzyme NotI recognition sequence and the 10-bp N-terminal sequence of the dockerin domain of the endo-β-1,4-glucanase-B gene. Using the synthesized primers, PCR was performed. As a result, a 1311-bp PCR band containing a chimeric kappa-carrageenase cCgkA gene fused with the dockerin domain gene of cellulase could be observed.

```
Primer SEQ ID NO: 8:
ccatggATTCTCAATCGGCTATTAAAAGTA

Primer SEQ ID NO: 9:
ggatccACGAACACTATGACGTGAATTTCT
```

Further, for cloning the chimeric beta-agarase cAgaB gene derived from Zobellia galactanivorans, with reference to a nucleotide sequence excluding a signal peptide region from the genomic DNA of Zobellia galactanivorans, primers were designed and synthesized such that a restriction enzyme SacI recognition sequence was inserted in the 5' end of the forward primer of SEQ ID NO: 10, and such that the 5' end of the reverse primer of SEQ ID NO: 11 contained the 10-bp N-terminal sequence of the dockerin domain of the endo-β-1,4-glucanase-B gene. Using the synthesized primers, PCR was performed. As a result, a 1201-bp PCR band containing a beta-agarase cAgaB gene derived from Pseudoalteromonas carrageenovora could be observed.

```
Primer SEQ ID NO: 10:
GCGCgagctcCGGCGACAATTCAAAATTTGATA

Primer SEQ ID NO: 11:
CAGCggatccTTTCTCTACAGGTTTATAGATC
```

In addition, for cloning the chimeric anhydro-galactosidase cAhgA gene derived from Zobellia galactanivorans, with reference to a nucleotide sequence excluding a signal peptide region from the genomic DNA of Zobellia galactanivorans, primers were designed and synthesized such that a restriction enzyme EcoRI recognition sequence was inserted in the 5' end of the forward primer of SEQ ID NO: 12, and such that the 5' end of the reverse primer of SEQ ID NO: 13 contained a restriction enzyme HindIII recognition sequence and the 10-bp N-terminal sequence of the dockerin domain of the endo-β-1,4-glucanase-B gene. As a result, a 1382-bp PCR band containing a chimeric anhydro-galactosidase cAhgA gene fused with the dockerin domain gene of cellulase could be observed.

```
Primer SEQ ID NO: 12:
GCGCgaattcGATGAACAAATACTCCCAATTTTTAAT

Primer SEQ ID NO: 13:
tgttaacatcTTGTTTTTTTACTCCTTTAGCTA
```

For cloning the mini-cellulose-binding protein A having one carbohydrate binding module (CBM) and two cohesin modules of cellulose-binding protein A which is the primary scaffolding subunit of Clostridium cellulovorans, with reference to the nucleotide sequence, primers were synthesized such that a restriction enzyme BamHI recognition sequence was inserted in the 5' end of the forward primer of SEQ ID NO: 14 and a restriction enzyme KpnI recognition sequence was inserted in the reverse primer of SEQ ID NO: 15. As a result, a 1647-bp PCR band containing a mCbpA gene, which is a portion of the cellulose-binding protein A gene derived from Clostridium cellulovorans, could be observed.

```
Primer SEQ ID NO: 14:
ggatccGCAGCGACATCATCAAT

Primer SEQ ID NO: 15:
GCGCggtaccGCTATAGGATCTCCAATATTTATT
```

Example 2: Cloning of Genes Fused with Dockerin Domain Gene of Cellulase

The amplification products of the dockerin domain gene of cellulase, and each of the CgkA, AgaB and AhgA genes, obtained in Example 1, were electrophoresed on 0.8% agarose gel, and the DNA fragments on the agarose gel were recovered using a gel extraction kit (GeneAll).

Next, in order to fuse the dockerin domain gene of cellulase with the kappa-carrageenase gene, the dockerin domain gene of cellulase with the beta-agarase gene, and the dockerin domain gene of cellulase with the anhydro-galactosidase gene, overlap PCR was performed using the recovered DNA fragments. From the two recovered DNA fragments, primers were designed and synthesized such that a restriction enzyme SacI recognition sequence was inserted in the 5' end of the forward primer of SEQ ID NO: 16 and such that a restriction enzyme NotI recognition sequence was inserted in the 5' end of the reverse primer of SEQ ID NO: 17. Using the synthesized primers, PCR was performed. As a result, a PCR band containing a 1311-bp chimeric kappa-carrageenase cCgkA gene derived from *Pseudoalteromonas carrageenovora*, fused with the dockerin domain gene of cellulase, could be observed.

```
Primer SEQ ID NO: 16:
ATATccatggATGCATCTATGCAACC

Primer SEQ ID NO: 17:
GCGCggatccATTCACCGCAAT
```

Furthermore, primers were designed and synthesized such that a restriction enzyme SacI recognition sequence was inserted in the 5' end of the forward primer of SEQ ID NO: 18 and such that a restriction enzyme SalI recognition sequence was inserted in 5' end of the reverse primer of SEQ ID NO: 19. Using the synthesized primers, PCR was performed. As a result, a PCR band containing a 1217-bp chimeric beta-agarase cAgaB gene derived from *Zobellia galactanivorans*, fused with the dockerin domain gene of cellulase, could be observed.

```
Primer SEQ ID NO: 18:
GCGCgagctcCGGCGACAATTCAAAATTTGATA

Primer SEQ ID NO: 19:
GCGCggccgcTCAATGATGATGATGATGATGTAAAAGCATTTTTTTAAG
```

Primers were designed and synthesized such that a restriction enzyme EcoRI recognition sequence was inserted in the 5' end of the forward primer of SEQ ID NO: 20 and such that a restriction enzyme Hind III recognition sequence was inserted in 5' end of the reverse primer of SEQ ID NO: 21. Using the synthesized primers, PCR was performed. As a result, a PCR band containing a 1382-bp chimeric anhydro-galactosidase cAhgA gene fused with the dockerin domain gene of cellulase, could be observed.

```
Primer SEQ ID NO: 20:
GCGCgaattcGATGAACAAATACTCCCAATTTTTAAT

Primer SEQ ID NO: 21:
GCGCaagcttTAAAAGCATTTTTTTAAGAACAGCTA
```

Next, each of the chimeric kappa-carrageenase cCgkA, chimeric beta-agarase cAgaB and chimeric anhydro-galactosidase cAhgA genes was digested with the respective restriction enzymes, and then ligated to the *E. coli* expression vector pET22b(+) which was then transformed into *E. coli* DH5α. Thereafter, the ligated recombinant plasmid DNAs were separated from the recombinant microorganisms. The recombinant vectors were named pET22(+)cCgkA, pET22(+)cAgaB and pET22(+)cAhgA, respectively (FIG. 1). Furthermore, the recombinant *E. coli* microorganisms were named DH5a/cCgkA, DH5a/cAgaB and DH5a/cAhgA, respectively.

Example 3: Measurement of Activity in Recombinant *E. coli* Microorganisms

Figure 2:
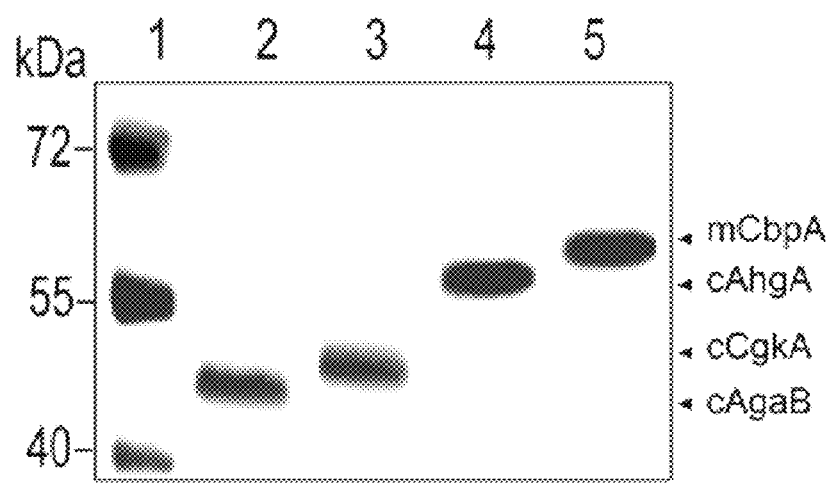
FIG. 2 shows the results of SDS-PAGE electrophoresis performed to confirm the sizes of the recombinant proteins expressed by the vectors pET22b(+)cCgkA, pET22b(+)cAgaB, pET22b(+)cAhgA and pET22b(+)mCbpA according to the present invention.

The recombinant *E. coli* microorganisms obtained in Example 2 were treated with IPTG so as to induce gene expression, and conditions enabling the cCgkA and cAgaB enzyme proteins to be secreted into culture medium were established. The microbial cells were shake-cultured at 28° C. for 90 minutes and centrifuged, and the proteins in the cells were degraded by sonication and concentrated (Millipore, amicon 10 kDa cut off) to obtain cCgkA and cAgaB enzyme proteins. However, regarding conditions enabling the cAhgA enzyme protein to be secreted into culture medium, the microbial cells containing cAhgA were shake-cultured at 16° C. (which is lower than that for cCgkA and cAgaB) for 240 minutes or more, and then centrifuged, and the protein in the cells was obtained by sonication. To confirm expression of the enzyme proteins in the resulting microorganisms, SDS-PAGE and Western blotting were performed. As a result, it was shown that the desired proteins were separated according to size (FIG. 2).

Example 4: Formation of Enzyme Complex of Enzyme Proteins with Mini-Scaffolding Protein A method for forming an enzyme complex of the purified enzymes (chimeric kappa-carrageenase cCgkA, chimeric beta-agarase cAgaB, and chimeric anhydro-galactosidase cAhgA) with mini-scaffolding protein mCbpA is as follows. To confirm the formation of a complex by binding of chimeric beta-agarase cAgaB from *Zobellia galactanivorans*, fused with the dockerin module of the endo-β-1,4-glucanase-B gene, with mini cellulose binding protein mCbpA, the four proteins were mixed with 100 µl of binding buffer at a specific ratio and incubated at low temperature, and then protein purification was performed using the interaction between a cellulose binding module (CBM) and cellulose, followed by analysis by Western blotting.

Figure 3A:
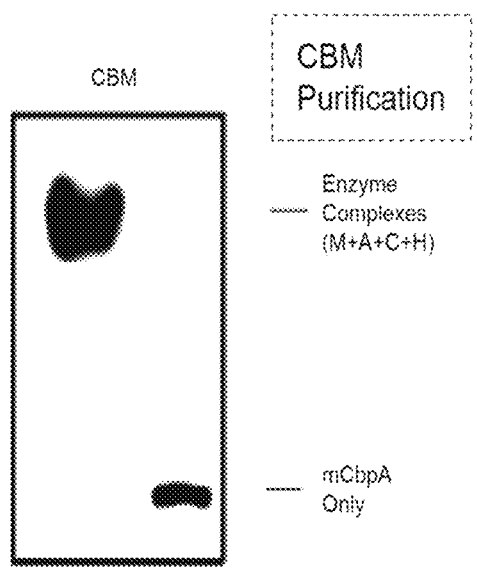
FIG. 3A shows the results of purification performed using the cellulose-binding module (CBM) of mini scaffold protein miniCbpA.
Figure 3B:
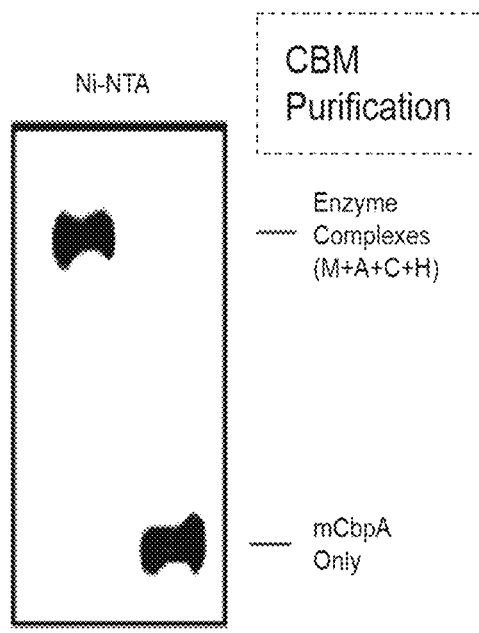
FIG. 3B shows the results of purification performed using Ni-NTA (nickel-nitrilotriacetic acid (NTA)). Furthermore.
Figure 3C:
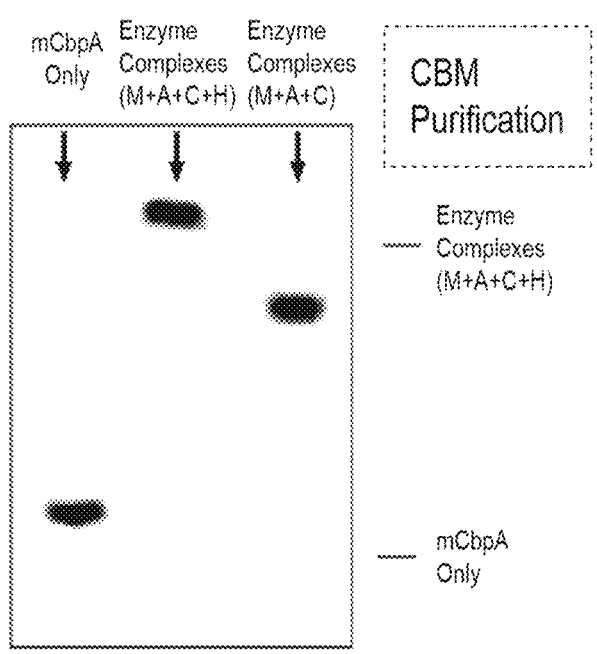
FIG. 3C shows the results of non-denaturing PAGE electrophoresis performed to confirm the sizes of enzyme complexes having various combinations of hydrolytic enzymes.

The binding buffer was composed of 25 mM sodium acetate buffer and 15 mM $CaCl_2$) [pH 6.0]. The enzyme proteins and the binding buffer were mixed at a ratio of 1:1:1:1:6=cAgaB:cCgkA:cAhgA:miniCbpA:binding buffer and allowed to react overnight (18 hours) at 4° C. On the next day, the reaction solution was analyzed by PAGE. For Western blotting analysis, anti-His-tag primary antibody (ELPIS) and goat anti-rabbit HRP conjugated (Santa Cruz) secondary antibody were used. Expression of the enzyme proteins was visualized with luminol reagent (Santa Cruz) (FIG. 3C).

Example 5: Purification of Enzyme Complex Using Carbohydrate Binding Module

For purification using a carbohydrate binding module (hereinafter referred to as CBM), the recombinant microorganism in an amount of 10 µg per ml of cellulose was shake-cultured at room temperature for 1 hour, and the CBM fusion protein bound to cellulose was centrifuged at 1,600 g for 10 minutes. The resulting material was washed with each of 20 mM Tris (pH 8.0) buffer containing 1M NaCl and 20 mM Tris (pH 7.5) buffer, and then eluted with 50 mM Tris (pH 12.5) buffer, and the sample was analyzed by SDS-PAGE (FIG. 3A).

Figure 4A:
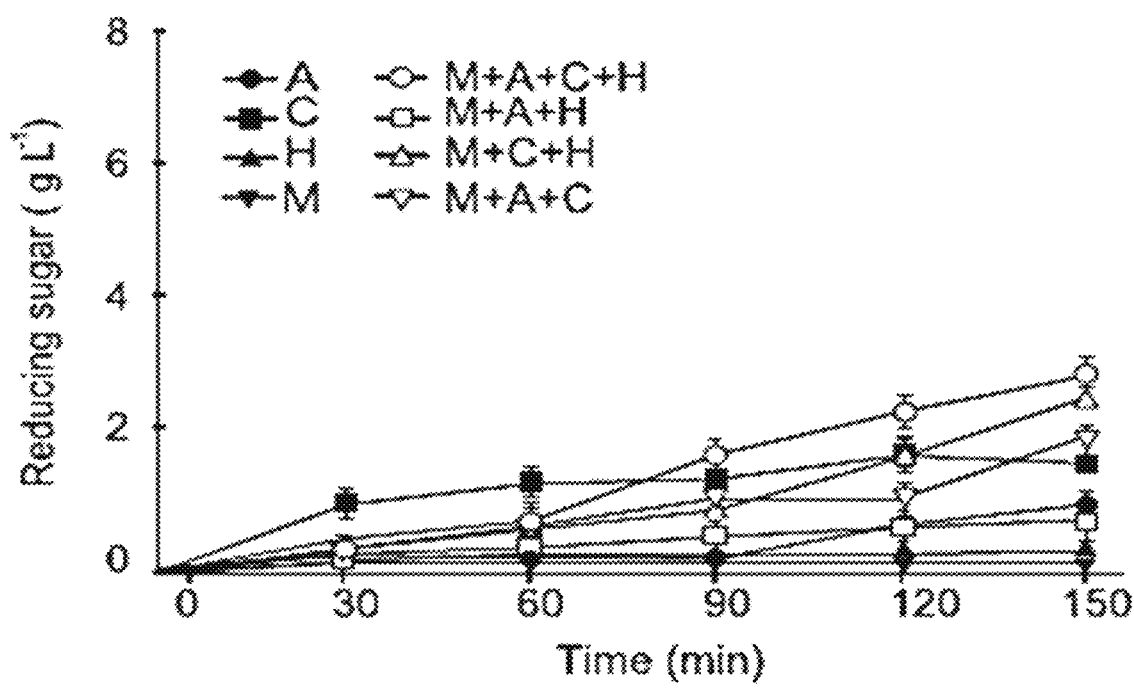
FIG. 4A shows the results of measuring reducing sugar production from carrageenan and agar substrates by use of enzyme complexes having various combinations of hydrolytic enzymes.

Example 6: Measurement of Reducing Sugar Production from Various Substrates by Use of Enzyme Complexes To test the degradation ability of the constructed hydrolytic enzyme complex, reducing sugar assay and 3,5-dinitrosalicylic acid (DNS) assay were performed. 0.5 ml of agar solution was mixed with 0.5 ml of carrageenan solution, and 0.5 ml of each of (i) an enzyme complex (CAM) containing chimeric kappa-carrageenase, chimeric beta-agarase, and mini cellulose-binding protein A, (ii) an enzyme complex (CHM) containing chimeric kappa-carrageenase, chimeric anhydro-galactosidase, and mini cellulose-binding protein A, (iii) an enzyme complex (AHM) containing chimeric beta-agarase, chimeric anhydro-galactosidase, and mini cellulose-binding protein A, and (iv) an enzyme complex (CAHM) containing chimeric kappa-carrageenase, chimeric beta-agarase, chimeric anhydro-galactosidase, and mini cellulose-binding protein A, was incubated at 50° C., and 0.075 ml of a sample was collected therefrom at 2-hour intervals. 0.15 ml of DNS solution was added to each sample, which was then heated for 10 minutes in a PCR system and cooled to room temperature, and the absorbance of the sample at 550 nm was measured (FIG. 4A).

Figure 4B:
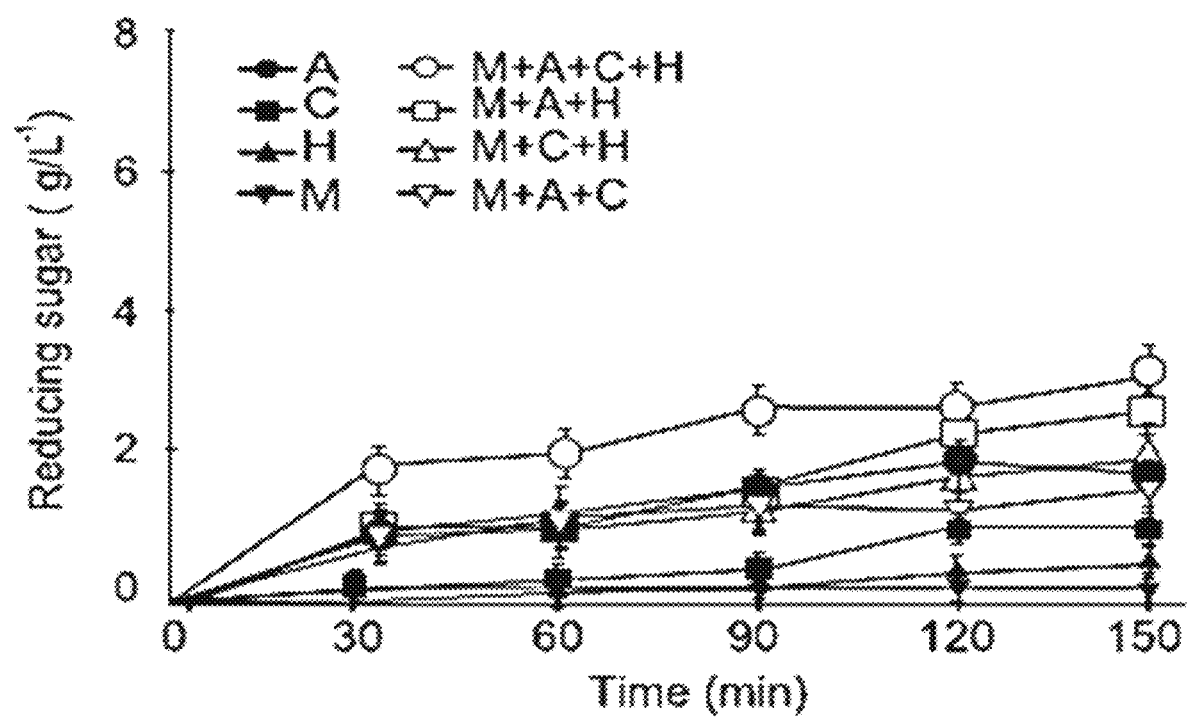
FIG. 4B shows the results of measuring reducing sugar production from an agar substrate by use of enzyme complexes having various combinations of hydrolytic enzymes. Furthermore.

In addition, to test the degradation ability of the constructed hydrolytic enzyme complex, reducing sugar assay and 3,5-dinitrosalicylic acid (DNS) assay were performed. 1.0 ml of agar solution and 0.5 ml of each of (i) an enzyme complex (CAM) containing chimeric kappa-carrageenase, chimeric beta-agarase, and mini cellulose-binding protein A, (ii) an enzyme complex (CHM) containing chimeric kappa-carrageenase, chimeric anhydro-galactosidase, and mini cellulose-binding protein A, (iii) an enzyme complex (AHM) containing chimeric beta-agarase, chimeric anhydro-galactosidase, and mini cellulose-binding protein A, and (iv) an enzyme complex (CAHM) containing chimeric kappa-carrageenase, chimeric beta-agarase, chimeric anhydro-galactosidase, and mini cellulose-binding protein A, were incubated at 50° C., and 0.075 ml of a sample was collected therefrom at 2-hour intervals. 0.15 ml of DNS solution was added to each sample, which was then heated for 10 minutes in a PCR system and cooled to room temperature, and the absorbance of the sample at 550 nm was measured (FIG. 4B).

Figure 4C:
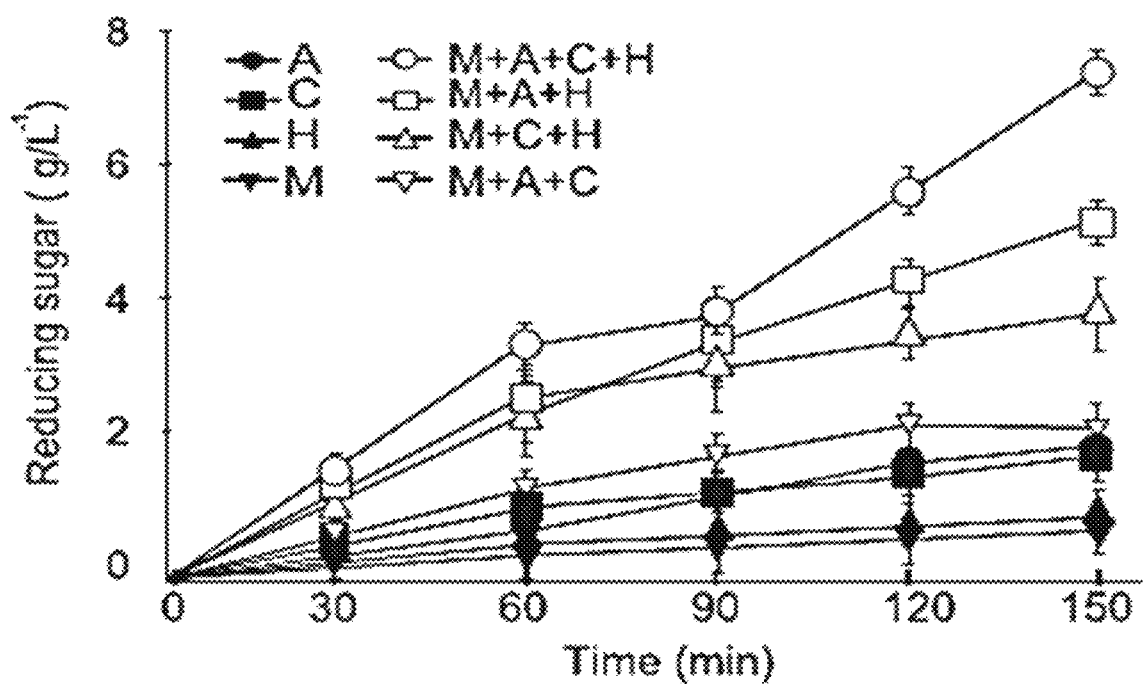
FIG. 4C shows the results of measuring reducing sugar production from a carrageenan substrate by use of enzyme complexes having various combinations of hydrolytic enzymes.
Figure 5A:
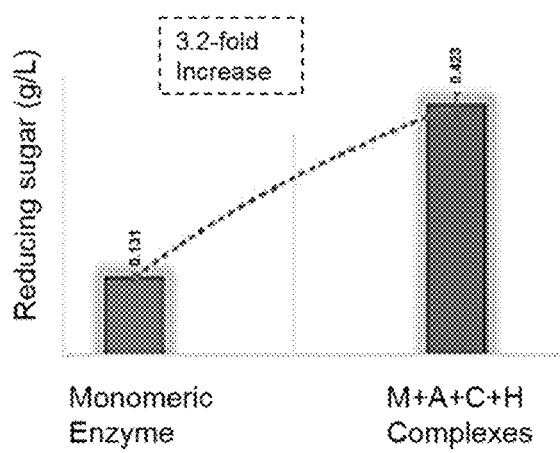
FIG. 5A shows the results of comparing reducing sugar production (average), obtained using a hydrolytic enzyme complex containing a combination of mCbpA, cCgkA, cAgaB, and cAhgA with reducing sugar production (average) obtained using monomeric enzyme, in agar and carrageenan substrates or an agar substrate or a carrageenan substrate
Figure 5B:
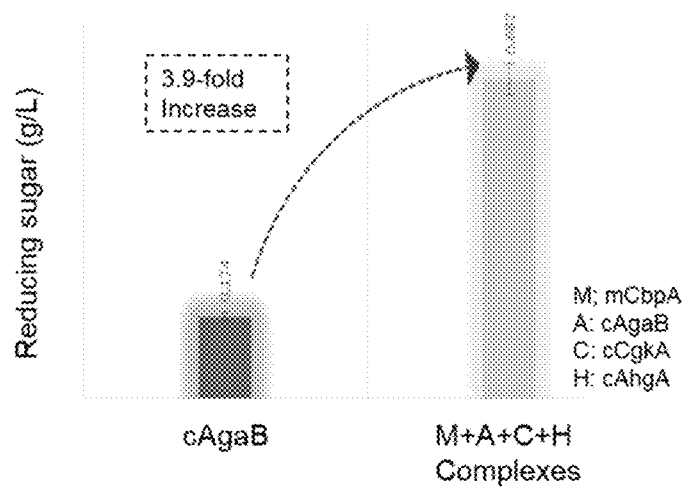
FIG. 5B shows the results of comparing reducing sugar production, obtained using a hydrolytic enzyme complex containing a combination of mCbpA, cCgkA, cAgaB, and cAhgA with reducing sugar production obtained using monomeric enzyme cAgaB in agar and carrageenan substrates.
Figure 6:
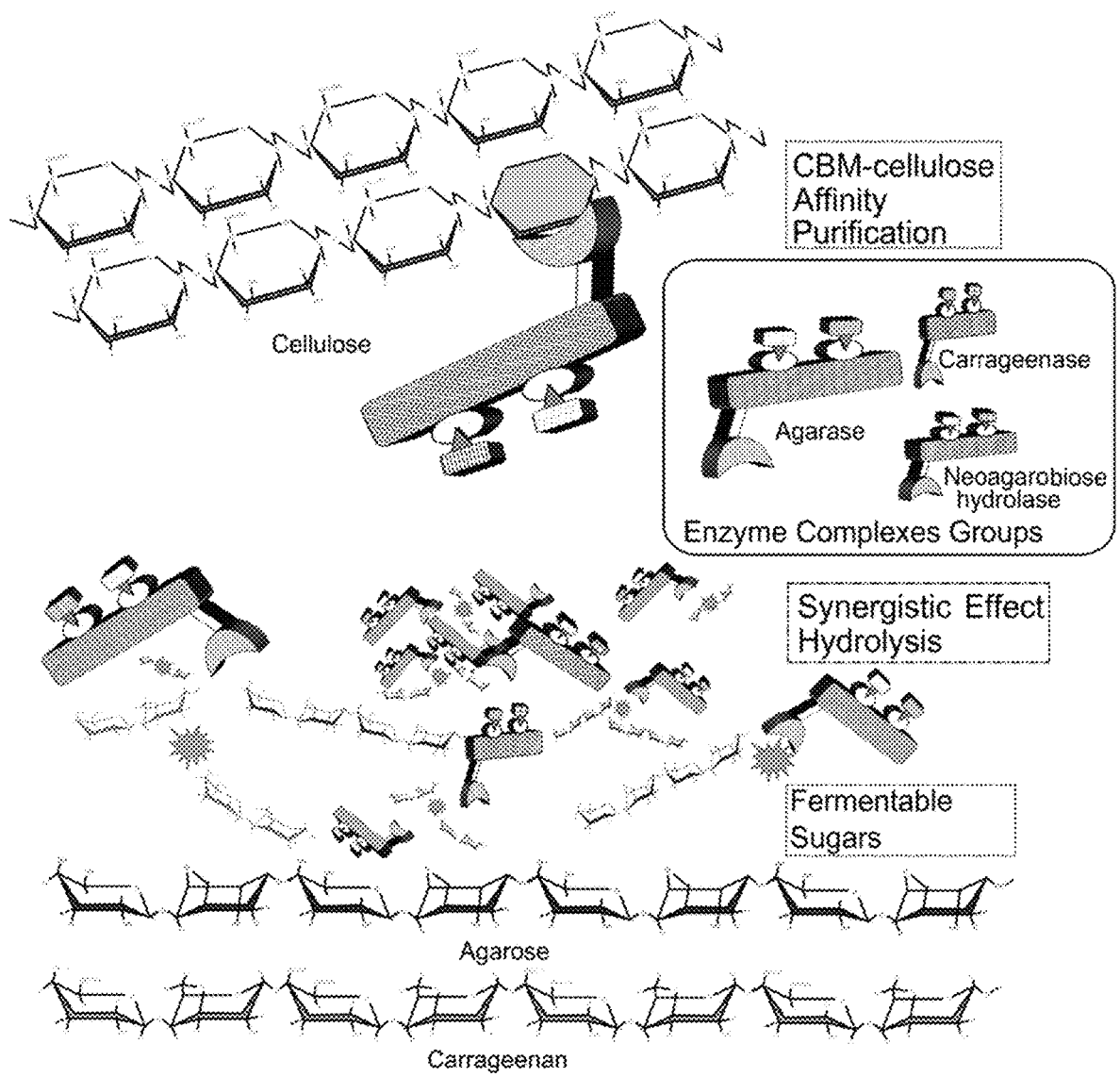
FIG. 6 shows an overall process scheme according to the present invention.

In addition, to test the degradation ability of the constructed hydrolytic enzyme complex, reducing sugar assay and 3,5-dinitrosalicylic acid (DNS) assay were performed. 1.0 ml of carrageenan solution and 0.5 ml of each of (i) an enzyme complex (CAM) containing chimeric kappa-carrageenase, chimeric beta-agarase, and mini cellulose-binding protein A, (ii) an enzyme complex (CHM) containing chimeric kappa-carrageenase, chimeric anhydro-galactosidase, and mini cellulose-binding protein A, (iii) an enzyme complex (AHM) containing chimeric beta-agarase, chimeric anhydro-galactosidase, and mini cellulose-binding protein A, and (iv) an enzyme complex (CAHM) containing chimeric kappa-carrageenase, chimeric beta-agarase, chimeric anhydro-galactosidase, and mini cellulose-binding protein A, were incubated at 50° C., and 0.075 ml of a sample was collected therefrom at 2-hour intervals. 0.15 ml of DNS solution was added to each sample, which was then heated for 10 minutes in a PCR system and cooled to room temperature, and the absorbance of the sample at 550 nm was measured (FIG. 4C).

INDUSTRIAL APPLICABILITY

According to the present invention, a degradation process employing an enzyme complex is applied for the production of agar degradation products, deviating from conventional methods that relied on physical and chemical pretreatment processes. Thus, the present invention will greatly contribute to efficiently converting marine algae into valuable products by use of a convenient, cost-effective, highly efficient and environmentally friendly degradation system while controlling the products.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. An enzyme complex in which the following (i) to (iv) are combined:
   (i) chimeric beta-agarase formed by a fusion of beta-agarase and the dockerin module of endo-β-1,4-glucanase-B;
   (ii) chimeric kappa-carrageenase formed by a fusion of kappa-carrageenase and the dockerin module of endo-β-1,4-glucanase-B;
   (iii) chimeric anhydro-galactosidase formed by a fusion of anhydro-galactosidase and the dockerin module of endo-β-1,4-glucanase-B; and
   (iv) mini cellulose-binding protein A.

2. The enzyme complex of claim 1, wherein the beta-agarase has the amino acid sequence of SEQ ID NO: 1.

3. The enzyme complex of claim 1, wherein the kappa-carrageenase has the amino acid sequence of SEQ ID NO: 2.

4. The enzyme complex of claim 1, wherein the anhydro-galactosidase has the amino acid sequence of SEQ ID NO: 3.

5. The enzyme complex of claim 1, wherein the endo-β-1,4-glucanase-B has the amino acid sequence of SEQ ID NO: 4.

6. The enzyme complex of claim 1, wherein the mini cellulose-binding protein A has the amino acid sequence of SEQ ID NO: 5.

7. A method of degrading red algal biomass, comprising a step of applying an enzymatic complex to red algal biomass, wherein the following components (i) to (iv) are combined in the enzymatic complex:
   (i) chimeric beta-agarase formed by a fusion of beta-agarase and the dockerin module of endo-R-1,4-ducanase-B;
   (ii) chimeric kappa-carrageenase formed by a fusion of kappa-carrageenase and the dockerin module of endo-R-1,4-ducanase-B;
   (iii) chimeric anhydro-galactosidase formed by a fusion of anhydro-galactosidase and the dockerin module of endo-R-1,4-ducanase-B; and
   (iv) mini cellulose-binding protein A.

* * * * *